(12) United States Patent
Wu et al.

(10) Patent No.: US 8,246,815 B2
(45) Date of Patent: Aug. 21, 2012

(54) METHODS FOR REGENERATION OF SOLVENTS FOR EXTRACTIVE PROCESSES

(75) Inventors: Kuang-Yeu Wu, Plano, TX (US); Tzong-Bin Lin, Chiayi (TW); Fu-Ming Lee, Katy, TX (US); Tsung-Min Chiu, Jhonghe (TW); Jyh-Haur Hwang, Dali (TW); Hung-Chung Shen, Chiayi (TW)

(73) Assignees: AMT International Inc., Plano, TX (US); CPC Corporation, Taiwan, Taipei (TW)

( * ) Notice: Subject to any disclaimer, the term of this patent is extended or adjusted under 35 U.S.C. 154(b) by 182 days.

(21) Appl. No.: 12/854,150

(22) Filed: Aug. 10, 2010

(65) Prior Publication Data

US 2012/0037542 A1     Feb. 16, 2012

(51) Int. Cl.
*C10G 51/02* (2006.01)

(52) U.S. Cl. ........ 208/321; 208/313; 208/325; 208/326; 208/330; 208/331; 208/333; 208/334

(58) Field of Classification Search ................. None
See application file for complete search history.

(56) References Cited

U.S. PATENT DOCUMENTS

| | | | |
|---|---|---|---|
| 3,037,062 A | 5/1962 | Gerhold | |
| 4,046,676 A | 9/1977 | Asselin | |
| 4,048,062 A | 9/1977 | Asselin | |
| 4,820,849 A | 4/1989 | Diaz | |
| 5,053,137 A | 10/1991 | Lal | |
| 5,382,746 A | 1/1995 | Child | |
| 5,877,382 A | 3/1999 | Eastman | |
| 7,666,299 B2 | 2/2010 | Wu | |
| 2009/0038991 A1 | 2/2009 | Wu | |
| 2010/0065504 A1 | 3/2010 | Yen | |
| 2010/0300830 A1 | 12/2010 | Noe | |
| 2010/0300939 A1 | 12/2010 | Noe | |

FOREIGN PATENT DOCUMENTS

| | | |
|---|---|---|
| EP | 0023370 A1 | 2/1981 |
| EP | 0555960 A2 | 8/1993 |
| WO | 2009/126127 A1 | 10/2009 |

OTHER PUBLICATIONS

International Search Report, PCT/US2011/043367, Date of Mailing: Oct. 19, 2011.

*Primary Examiner* — Tam M Nguyen
(74) *Attorney, Agent, or Firm* — Cascio & Zervas

(57) ABSTRACT

An improved solvent regeneration system for extractive distillation and liquid-liquid extraction processes capable of effectively removing heavy hydrocarbons and polymeric materials that otherwise develop in a closed solvent loop. The improved process employs a light hydrocarbon displacement agent, which is at least partially soluble in the solvent to squeeze the heavy hydrocarbons and polymeric materials out of the solvent, with virtually no additional energy requirement. It has been demonstrated that the light non-aromatic hydrocarbons in the raffinate stream generated from the extractive distillation or the liquid-liquid extractive process for aromatic hydrocarbons recovery can displace not only the heavy non-aromatic hydrocarbons but also the heavy aromatic hydrocarbons from the extractive solvent, especially when the aromatic hydrocarbons in the solvent are in the $C_{10+}$ molecular weight range.

34 Claims, 5 Drawing Sheets

METHODS FOR REGENERATION OF SOLVENTS FOR EXTRACTIVE PROCESSES

FIELD OF THE INVENTION

The present invention relates generally to novel methods of regenerating solvents from solvent-rich streams. The methods are suited for recovering extractive solvents in extractive distillation and liquid-liquid extraction processes and particularly from mixtures containing polar and less polar hydrocarbons, measurable amounts of hydrocarbons that are heavier than intended feedstock, and/or polymeric materials that are generated in these processes. The methods can effectively remove and recover heavy hydrocarbons from a closed solvent loop operating under mild conditions with no additional process energy.

BACKGROUND OF THE INVENTION

For many years, liquid-liquid extraction (LLE) using sulfolane or polyalkylene glycol as the extractive solvent has been the most important commercial process for purifying the full-range ($C_6$-$C_8$) of aromatic hydrocarbons from petroleum streams, including reformate, pyrolysis gasoline, coke oven oil, and coal tar. Extractive distillation (ED) with N-methylpyrrolidone as the extractive solvent has also been extensively applied for benzene recovery from coal tar and coke oven oil. Recently, ED using sulfolane solvent became commercially viable for benzene and toluene recovery from reformate or pyrolysis gasoline after $C_{8+}$ fractions are removed from the feedstock. The extractive solvent in both ED and LLE processes for aromatics recovery is internally circulated indefinitely in the process system in a closed loop.

Typically, the ED or LLE feedstock is fed to a prefractionation column for removing the heavy portion and leaving only the desirable portion to be fed to the ED column or LLE column. Even for well-designed prefractionation columns, under reasonable operating conditions, some measurable amount of heavy hydrocarbons will slip into the feed stream to the ED or LLE process. And under poorly operated or malfunctioned prefractionation columns, the amount of heavy hydrocarbons in the feed stream increases significantly. Subsequently, the concentration of heavy hydrocarbons as well as polymeric materials, which are generated by the interactions among the heavy hydrocarbons, decomposed solvent, solvent additives and species from equipment corrosion, can increase quickly, thereby deteriorating solvent performance. In severe cases, it could render the process inoperable.

U.S. Pat. No. 4,820,849 to Diaz describes a process for reducing the level of corrosive impurities in sulfolane solvent originating from a process for the extraction of aromatic hydrocarbons from petroleum, having a pH of at least 8.5. The process combines a sulfolane-soluble polyprotic acidic substance with the sulfolane to form a solid phase containing at least a portion of the corrosive impurities and separates the sulfolane from the solid phase. The polyprotic acidic substance is sulfuric acid or phosphoric acid. The method is tedious and requires acid addition and solids handling, and deals with only the corrosive impurities in the solvent. It is not applicable for the removal of heavy hydrocarbons or polymeric materials. A regeneration and/or purification method disclosed in U.S. Pat. No. 5,053,137 to Lal uses a pair of columns arranged in series, with the first column containing cation exchanger resin and the second containing anion exchanger resin, to remove ionic and polar impurities from the solvent (sulfolane).

To remove heavy hydrocarbons and polymeric materials and polar impurities derived from oxidized solvent, a method applied extensively in commercial LLE or ED processes employs a thermal solvent regenerator, where a small slip stream, of lean solvent (approximately 1-2% of total lean solvent stream) is heated with or without stripping steam in order to recover the regenerated solvent or any heavy, components having boiling points lower that of the solvent. The heavy polymeric materials, having boiling point higher than that of the solvent, are removed from the bottom of the solvent regenerator as sludge. The basic concepts of this thermal solvent regeneration scheme are described in U.S. Pat. Nos. 4,046,676 and 4,048,062 both to Asselin in relationship to a LLE process for aromatics recovery where a portion of lean solvent from the bottom of the solvent recovery column (SRC) is diverted into a solvent regeneration zone. A vaporous stripping medium (steam) is introduced into the solvent regeneration zone separately, recovered with regenerated solvent and introduced into the SRC as at least a portion of the stripping steam. When applied to LLE processes using sulfolane/water, or polyalkylene glycol/water as the extractive solvent, thermal solvent regeneration has been commercially successful in keeping the heavy hydrocarbons and polymeric materials at a tolerable level in the lean solvent. This is because a significant amount of heavy hydrocarbons ($C_9$-$C_{12+}$) in the feedstock is rejected by the solvent phase in the LLE column and is removed with the raffinate phase as a part of the non-aromatic product. For the same type of molecules, the higher the boiling point, the lower the polarity. Among the heavy hydrocarbons, only $C_{9+}$ aromatic compounds are likely to be extracted by the solvent, which can be almost entirely stripped from the solvent in the SRC under normal operating conditions.

In a normal ED process for aromatics recovery, however, all of the heavy hydrocarbons tend to remain in the rich solvent at the bottom of extractive distillation column (EDC) due to their high boiling points. Even for the narrow boiling-range ($C_6$-$C_7$) feedstock for benzene and toluene recovery, there can be 3-5% heavy hydrocarbons trapped in the solvent, in spite of increase in the severity of the SRC (higher temperature and vacuum level, and more stripping steam) to drive additional heavies from the lean solvent. For the full boiling-range ($C_6$-$C_8$) feedstock for benzene, toluene and xylene recovery, however, the boiling points of most heavy hydrocarbons are too high to be stripped from the solvent in the SRC and consequently they accumulate in the solvent since the solvent is circulated between the EDC and the SRC indefinitely in a closed loop.

The above described solvent regeneration schemes are not suitable for the ED processes since they were designed specifically for LLE processes for removing relatively minor amounts of polymeric materials formed possibly from the reactions between the oxidized or decomposed solvent components and trace of the heavy hydrocarbons in the solvent. Indeed, when these solvent regeneration schemes were implemented with ED processes, heavy hydrocarbons tend to accumulate and polymerize in the closed solvent loop. This buildup continues until the polymerized materials achieve boiling points higher than that of sulfolane (>287° C.), whereupon they exit the closed loop through the bottom of the solvent regenerator. It is a potentially disastrous situation since excessive polymeric materials in the solvent not only significantly changes the solvent properties (selectivity and solvency), but also plugs process equipment, such as, pumps, valves, column internals, lines, etc., to render the ED process inoperable.

To take advantage of the fact that most extractive solvents for ED and LLE are water soluble, U.S. Pat. No. 7,666,299 to Wu adopts a different approach for removing heavy hydrocarbons from the extractive solvent whereby lean solvent is introduced into a low temperature, energy saving and easy-to-operate solvent washing zone and contacted with a stream of process water, which is circulated in closed loop. Solvent is dissolved into the water phase, while heavy hydrocarbons are rejected by water and accumulated into the hydrocarbon phase. At a minimum, the solvent washing zone serves as a decanter to remove and separate the minor heavy hydrocarbon phase from the bulk water phase. The decanted hydrocarbon phase accumulates and is withdrawn from top of the decanter periodically. In one configuration, the washing water contacts lean solvent in a counter-current fashion to extract the solvent into the water phase and to reject the heavy hydrocarbons and other water-insoluble into the oil phase. The water phase containing essentially the purified solvent is withdrawn continuously from the lower portion of the contactor. A minor hydrocarbon phase accumulates at the top of the contactor and is removed periodically from the contactor under level control. Any solids precipitation formed in the solvent washing zone is removed from the bottom of the contactor. Since this method requires a significant amount of water, it may be difficult to balance and distribute the process water in the closed system.

SUMMARY OF THE INVENTION

The present invention is directed to an improved solvent regeneration system for ED and LLE processes that is capable of effectively removing heavy hydrocarbons and polymeric materials that otherwise develop in a closed solvent loop. The invention is based in part on the demonstration that the light non-aromatic hydrocarbons in the raffinate stream generated from the ED or the LLE process for aromatic hydrocarbons recovery can displace not only the heavy non-aromatic hydrocarbons but also the heavy aromatic hydrocarbons from the extractive solvent, especially when the heavy aromatic hydrocarbons in the solvent are in the $C_{10+}$ molecular weight range. The inventive process does not require water to extract the solvent away from the heavy hydrocarbons and impurities in order to purify the solvent, rather a more polar hydrocarbon referred to as "the displacement agent," which is at least partially soluble in the solvent, is employed to "squeeze" the less polar heavy materials out of the solvent.

In one aspect, the invention is directed to a method for recovering a polar hydrocarbon selective solvent substantially free of hydrocarbons and other impurities from a solvent-rich stream containing the selective solvent, measurable amounts of heavy hydrocarbons, and polymeric materials generated from reactions among thermally decomposed or oxidized solvent, heavy hydrocarbons, and additives, which method includes the steps of:

(a) introducing a feed containing polar and less polar hydrocarbons into a middle portion of an extractive distillation column (EDC) and introducing a solvent-rich stream into an upper portion of the EDC as a selective solvent feed;

(b) recovering a water-containing, less polar hydrocarbon-rich stream from a top of the EDC and withdrawing a first solvent-rich stream containing solvent, polar hydrocarbons, and measurable amounts of heavy hydrocarbons and polymeric materials from a bottom of the EDC;

(c) introducing the first solvent-rich stream into a middle portion of a solvent recovery column (SRC), recovering a polar hydrocarbon-rich stream, that is substantially free of solvent and less polar hydrocarbons, from a top of the SRC, and removing a second solvent-rich stream from a bottom of the SRC;

(d) introducing a first portion of the second solvent-rich stream into the upper portion of the EDC in step (a) as the selective solvent feed;

(e) cooling a second portion of the second solvent-rich stream in step (c) and introducing the cooled second portion of the solvent-rich stream into an upper portion of a solvent cleanup zone to form a solvent phase;

(f) introducing a light hydrocarbon-rich stream into a lower portion of the solvent cleanup zone, as a heavy hydrocarbon displacement agent, to squeeze out heavy hydrocarbons and polymeric materials from the solvent phase into a hydrocarbon phase;

(g) withdrawing an accumulated hydrocarbon phase containing heavy hydrocarbons and polymeric materials from an upper portion of the solvent cleanup zone, and recovering a solvent phase containing solvent and light hydrocarbons, which serve as heavy hydrocarbon displacement agents, and having has substantially reduced levels of heavy hydrocarbons and polymeric materials, from a lower portion of the solvent cleanup zone; and (h) introducing the solvent phase from the solvent cleanup zone in step (g) into an upper portion of the EDC in step (a) as part of a selective solvent feed to recycle purified solvent into a solvent loop.

In a preferred embodiment, step (d) comprises introducing a greater portion of the second solvent-rich stream into an upper portion of the EDC and introducing a first minor portion of the second solvent-rich stream into an upper portion of a high temperature thermal solvent regeneration zone, recovering a third solvent-rich stream containing solvent, water, and hydrocarbons and other compounds having boiling points below that of the solvent, from a top of the solvent regeneration zone, and removing heavy sludge from a lower portion of the solvent regeneration zone and wherein step (e) comprises cooling a mixture that comprises the third solvent-rich stream in step (d) and a second minor portion of the second solvent-rich stream in step (c) and introducing the mixture into an upper portion of the solvent cleanup zone to form a solvent phase.

In another aspect, the invention is directed to a method for recovering a polar hydrocarbon selective solvent substantially free of hydrocarbons and other impurities from a solvent-rich stream containing the selective solvent, measurable amount of heavy hydrocarbons, and polymeric materials generated from reactions among thermally decomposed or oxidized solvent, heavy hydrocarbons, and additives, which method includes the steps of:

(a) introducing a feed containing polar and less polar hydrocarbons into a middle portion of a liquid-liquid extraction column (LLE) and introducing a solvent-rich stream into an upper portion of the LLE as a selective solvent feed;

(b) recovering a water-containing, less polar hydrocarbon-rich stream from a top of the LLE and withdrawing the first solvent-rich stream containing solvent, polar hydrocarbons, minor amounts of less polar hydrocarbons, and measurable amounts of heavy hydrocarbons and polymeric materials from a bottom of the LLE;

(c) introducing a mixture of comprising the first solvent-rich stream and a minor portion of a third solvent-rich stream from a bottom of a solvent recovery column (SRC), into an upper portion of an extractive stripping column (ESC), recovering a hydrocarbon-rich, vapor containing less polar hydrocarbons and a significant amount of benzene and heavier aromatics, which is condensed and recycled to a lower portion of LLE as the reflux, and withdrawing a second solvent-rich stream containing solvent, polar hydrocarbons which is substantially free of less polar hydrocarbons, and measurable amounts of heavy hydrocarbons and polymeric materials from a bottom of the ESC;

(d) introducing the second solvent-rich stream in step (c) into a middle portion of the SRC, withdrawing a polar hydrocarbon-rich stream, which is substantially free of solvent and non-polar hydrocarbons, from a top of the SRC, and removing a third solvent-rich stream from the bottom of the SRC;

(e) introducing a portion of the third solvent-rich stream into the upper portion of the LLE in step (a) as the selective solvent feed;

(f.) cooling a minor portion of the third solvent-rich stream in step (d) and introducing the cooled minor portion of the third solvent-rich stream into an upper portion of a solvent cleanup zone to form a solvent phase;

(g) introducing a light hydrocarbon-rich stream into a lower portion of the solvent clean-up zone, as a heavy hydrocarbon displacement agent, to squeeze out heavy hydrocarbons and polymeric materials from the solvent phase into a hydrocarbon phase;

(h) withdrawing an accumulated hydrocarbon phase containing heavy hydrocarbons and polymeric materials from an upper portion of the solvent clean-up zone and recovering the solvent phase containing solvent, light hydrocarbons, which serve as heavy hydrocarbon displacement agents, and having substantially reduced levels of heavy hydrocarbons and polymeric materials, from a lower portion of the solvent clean-up zone; and (i) introducing the solvent phase from the solvent clean-up zone in step (h) into an upper portion of the LLE in step (a) as part of a selective solvent feed to recycle purified solvent into a solvent loop.

In a preferred embodiment, step (e) comprises introducing a greater portion of the third solvent-rich stream into the upper portion of the LLE in step (a) and introducing a first minor portion of the third solvent-rich stream into an upper portion of a high-temperature thermal solvent regeneration zone, recovering a fourth solvent-rich stream containing solvent, water, and hydrocarbons and other compounds having boiling points below that of the solvent, from a top of the solvent regeneration zone, and removing heavy sludge from a lower portion of the solvent regeneration zone and wherein step (f) comprises cooling a mixture comprising the fourth solvent-rich stream in step (e) and a second minor portion of the third solvent-rich stream in step (d) and introducing the mixture into an upper portion of the solvent cleanup zone to form a solvent phase.

The present invention provides improved solvent regeneration systems for ED process and LLE processes to significantly reduce the amount of heavy ($C_9$-$C_{12}$) hydrocarbons strapped in the closed solvent loop, and thus improve the solvent performance, reduce the amount of (or even eliminate altogether the) solvent to be treated in the conventional thermal regenerator per cycle, and recover the value of heavy hydrocarbons, as well as save process energy.

With the inventive ED process, improved benzene recovery can be achieved by allowing an increased amount of $C_{9+}$ hydrocarbons to slip into the rich solvent with the aromatics in the bottom of ED column, since the $C_{9+}$ hydrocarbons can be removed and recovered from the closed solvent loop. The inventive process does not require a xylene column, which is typically employed in the prior art to separate the xylene product from the $C_{9+}$ hydrocarbons in the aromatic product section of an ED or LLE process, which saves process energy and reduces overall operating costs. This is accomplished, in part, by keeping substantially all the $C_{9+}$ hydrocarbons at the bottom of the SRC with the lean solvent, which can be removed and recovered from the closed solvent loop. Similarly, since olefinic hydrocarbons are more concentrated in the heavy hydrocarbons fraction, with substantially all the $C_{9+}$ hydrocarbons kept at the bottom of the SRC with the lean solvent, the invention significantly reduces the load of a clay tower or other system for removing olefinic hydrocarbons from the aromatic product.

DETAILED DESCRIPTION OF PREFERRED EMBODIMENTS

The techniques of the present invention can be integration into an ED or LLE process for the selective separation and recovery of polar hydrocarbons from a mixture containing the polar hydrocarbons and less polar hydrocarbons. The inventive processes will be described in relation to the separation and recovery of aromatic hydrocarbons from mixtures containing aromatics and non-aromatics, including paraffins, iso-paraffins, naphthenes, and/or olefins, but it is understood that the techniques are applicable to a multitude of hydrocarbon mixtures.

Figure 1:
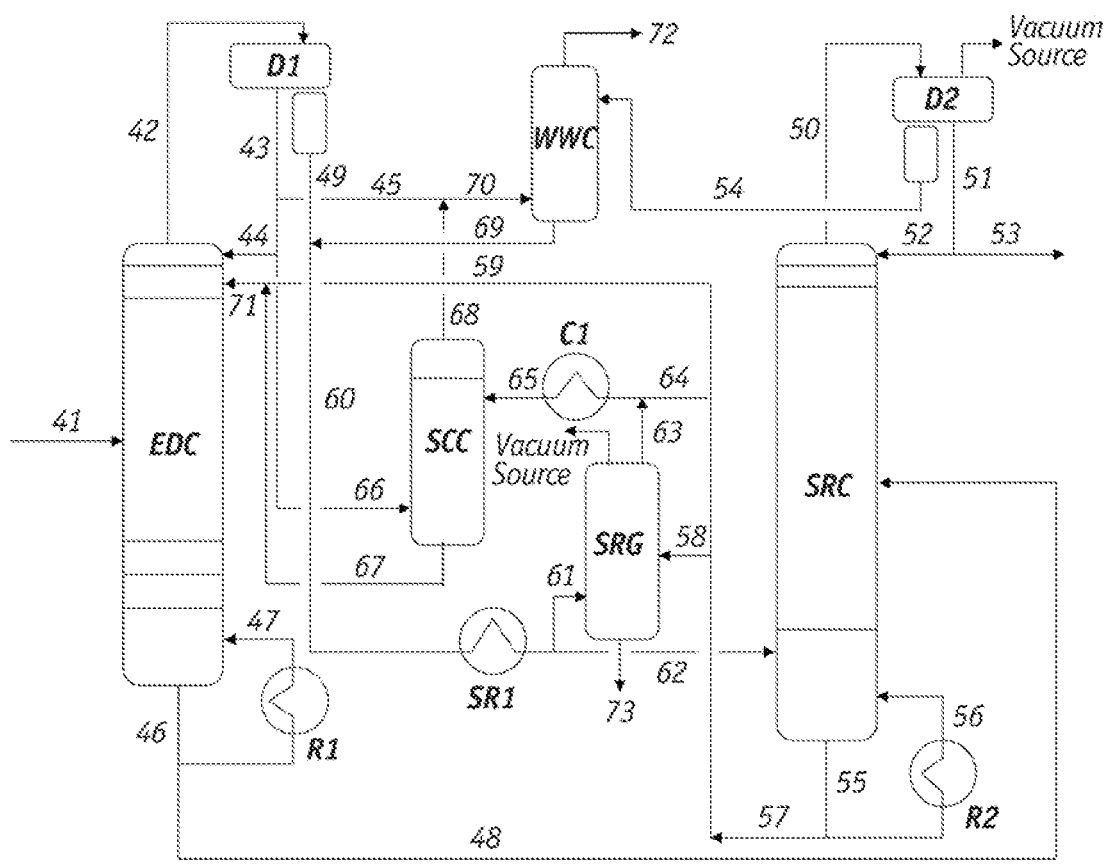
FIG. 1 is a schematic diagram of a process for aromatic hydrocarbons recovery from mixtures of aromatic and non-aromatic hydrocarbons through an ED process in which the solvent is regenerated through a thermal solvent regenerator in combination with a solvent clean-up column using the raffinate from an overhead of an ED column as the displacement agent.
Figure 3:
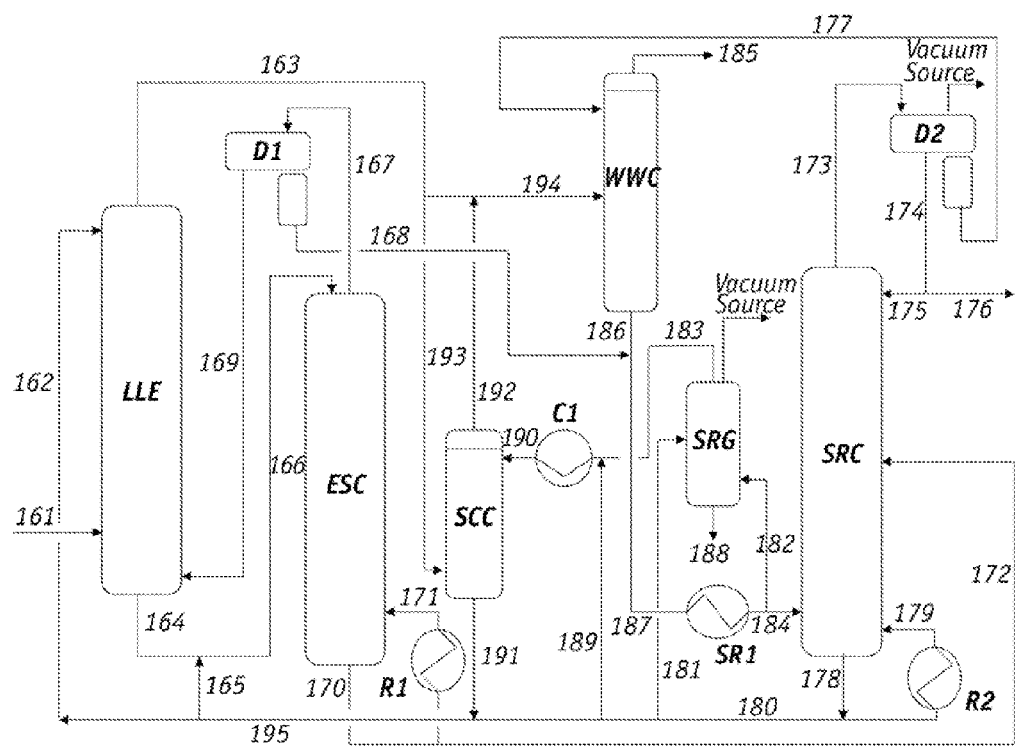
FIG. 3 is a schematic diagram of a process for aromatic hydrocarbons recovery from mixtures of aromatic and non-aromatic hydrocarbons through a LLE process in which the solvent is regenerated through a thermal solvent regenerator in combination with a solvent clean-up column using the raffinate from a LLE column as the displacement agent.

In one embodiment of the invention for aromatic hydrocarbon recovery, as depicted in FIGS. 1 and 3, a portion of the lean solvent in an ED or LLE process, which contains measurable amounts of heavy hydrocarbons and polymeric materials, is withdrawn from the bottom of a SRC and combined with regenerated solvent from an overhead of a thermal solvent regenerator. The combined stream is introduced into a low temperature, energy saving and easy-to-operate solvent clean-up zone after cooling. The solvent-clean-up zone (or solvent clean-up column) preferably consists of a column with trays, packings, and/or rotating discs, or a pulse column. A raffinate stream from the overhead of the ED column in the ED process (or the overhead of the LLE column in the LLE process) is also introduced into the solvent clean-up zone, to contact the combined solvent stream. At a minimum, the solvent clean-up zone serves as a phase separator, for instance, in the form of a settling tank or decanter, to remove and separate the hydrocarbon phase containing the "squeezed" out heavy hydrocarbons and polymeric materials from the solvent phase and yield a solvent phase which contains only light non-aromatics (the displacement agents) and substantially reduced heavy hydrocarbons. The separated hydrocarbon phase is continuously withdrawn from top of the phase separator. Alternatively, the solvent clean-up zone can comprise a static mixer for mixing the raffinate and solvent streams and a phase separator into which the mixed composition is transferred and allowed separate.

Preferably, the raffinate (which contains the displacement agent) contacts the combined solvent stream in a counter-current fashion in order to squeeze out the heavy hydrocarbons and polymeric materials from the solvent phase and into the hydrocarbon phase. The solvent phase, which essentially contains solvent, the light displacement agent (light non-aromatics) and much reduced levels of heavy hydrocarbons and polymeric materials, is withdrawn continuously from the lower portion of the contactor and fed into the ED column (or the LLE column of a LLE process), as a part of the lean solvent feed to this column as a way to recycle purified solvent into the closed solvent loop. A hydrocarbon phase from the top of the contactor is removed continuously from the contactor preferably under level control and fed to a water wash column to remove any solvent in the hydrocarbon phase.

Alternatively, any benzene-free, light hydrocarbon mixture can be used as the displacement agent to remove heavy hydrocarbons and polymeric materials from the lean solvent. With the present invention, the incorporation of a solvent clean-up zone to remove a substantial portion of the heavy hydrocarbons and polymeric materials will greatly reduces the loading requirements of the thermal solvent regenerator, when the latter is employed, and renders the process easier to operable, especially for the ED process.

Figure 2:
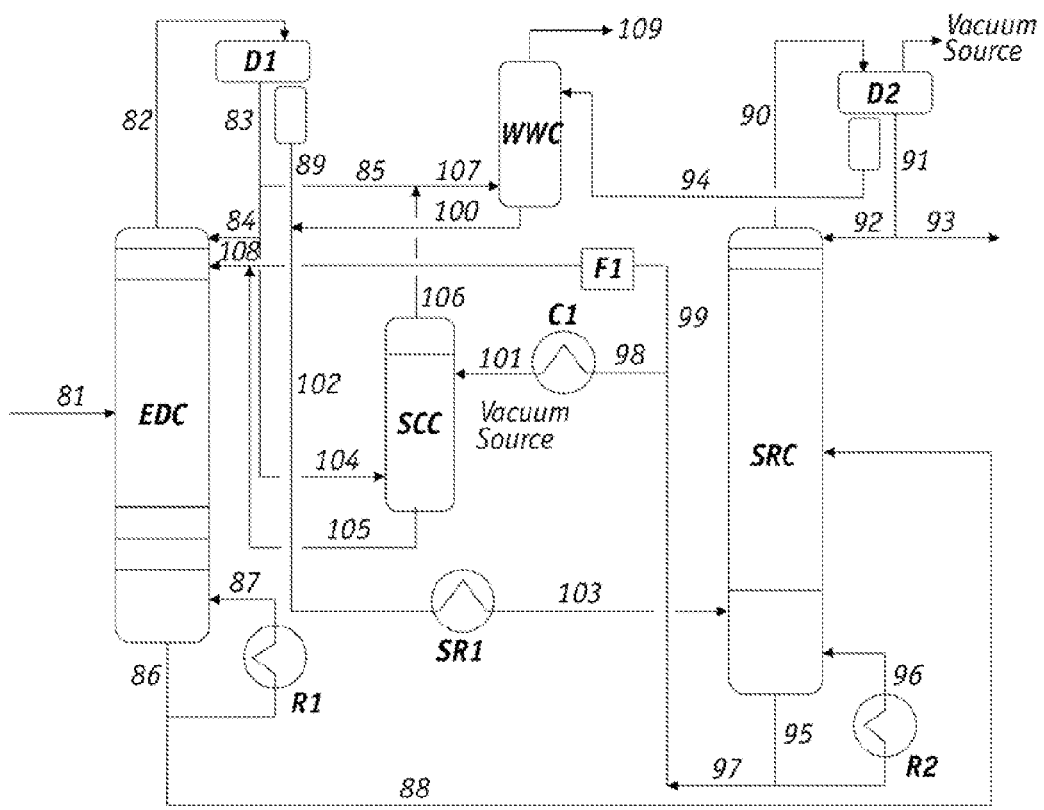
FIG. 2 is a schematic diagram of a process for aromatic hydrocarbons recovery from mixtures of aromatic and non-aromatic hydrocarbons through an ED process in which the solvent is regenerated through a solvent clean-up column alone using the raffinate from an overhead of an ED column as the displacement agent.
Figure 4:
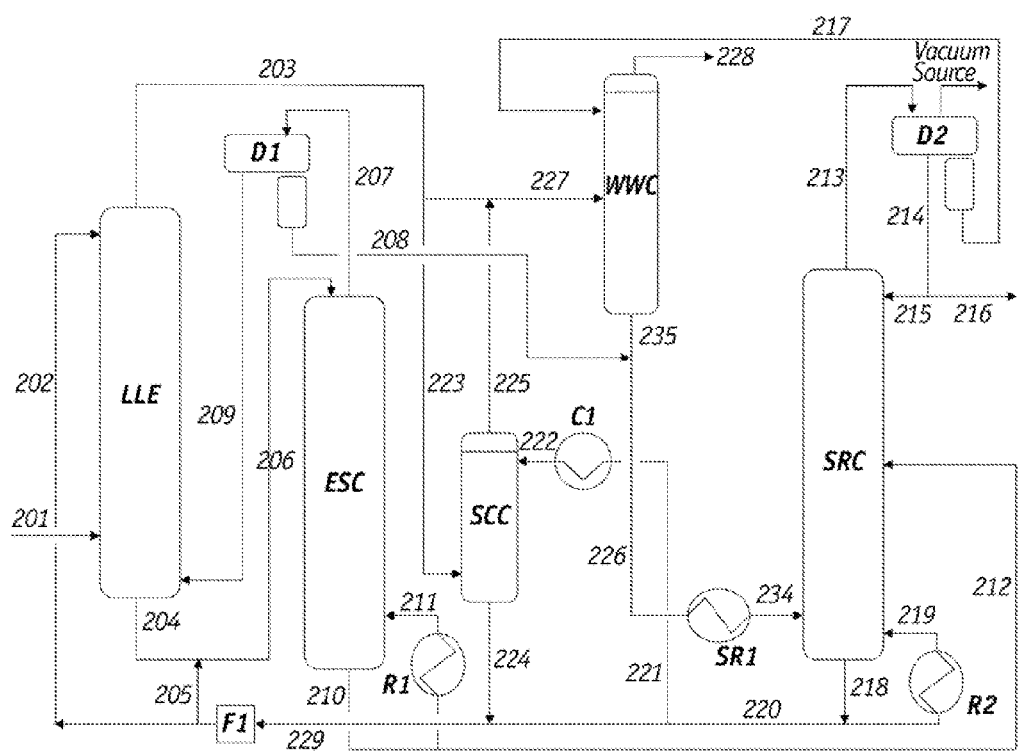
FIG. 4 is a schematic diagram of a process for aromatic hydrocarbons recovery from mixtures of aromatic and non-aromatic hydrocarbons through a LLE process in which the solvent is regenerated through a solvent clean-up column alone using the raffinate from a LLE column as the displacement agent.

In another embodiment of the invention, as depicted in FIGS. 2 and 4, a solvent regeneration scheme employs an efficient, low temperature and energy-saving solvent clean-up system. The process does not require any high temperature and energy-intensive thermal solvent regenerator. A portion of a lean solvent stream that is withdrawn from the bottom of a SRC is diverted and introduced into a solvent clean-up zone after cooling. A portion of a raffinate, which is collected from the overhead of the ED column (or from the overhead of the LLE column in a LLE process), is introduced into the solvent clean-up zone, to contact a diverted lean solvent stream. At a minimum, the solvent clean-up zone can serve as a phase separator, for instance in the form of a settling tank or decanter, to remove and separate the hydrocarbon phase containing the "squeezed" out heavy hydrocarbons and polymeric materials from the solvent phase, to yield a solvent phase containing only light non-aromatics (the displacement agents) and substantially reduced levels of heavy hydrocarbons and polymeric materials. The separated hydrocarbon phase is continuously withdrawn from top of the phase separator.

The solvent clean-up operation is typically conducted in a continuous multi-stage contacting device, and preferably in one that is designed for counter-current extraction. Suitable designs include columns with trays, columns with packings, columns with rotating discs, pulse columns, multi-stage mixers/settlers, and any other rotating type contactors. Alternatively, the solvent clean-up zone can comprise a static mixer for mixing the raffinate and solvent streams and a phase separator into which the mixed composition is transferred and allowed separate. Preferably, the displacement agent contacts the lean solvent in a counter-current fashion to "squeeze out" the heavy hydrocarbons and polymeric materials from the solvent phase into the hydrocarbon phase. The solvent phase containing essentially the solvent, light non-aromatic hydrocarbons (the displacement agent) and much reduced levels of heavy hydrocarbons, is withdrawn continuously from the bottom of the contactor and fed to the ED or LLE column as a part of the lean solvent feed. The hydrocarbon phase containing the "squeezed" heavy hydrocarbons and polymeric materials is accumulated on the top of the contactor and is removed periodically from the contactor under interface level control. Alternatively, any benzene-free, light hydrocarbon mixture can be used as the displacement agent to remove heavy hydrocarbons and polymeric materials from the lean solvent. Optionally, a filter, preferably one that is enhanced with a magnetic field, can be installed in the solvent loop to selectively remove paramagnetic species generated from the interaction of decomposed solvent with various solvent additives as well as the heavy hydrocarbons. Suitable filters with magnets are described in US Pub. No. 20100065504 to Yen et al.

In the above-described preferred embodiments, due to the fact that the $C_{9+}$ heavy hydrocarbons are recovered from the lean solvent in the solvent clean-up zone, the ED column in the ED process is preferably operated under such conditions as to maximize the benzene recovery by keeping substantially all $C_{9+}$ hydrocarbons in the bottom of the ED column with the rich solvent (extract) stream. The SRC is preferably operated under such conditions as to strip only $C_8$ and lighter hydrocarbons from the rich solvent stream and to keep substantially all $C_9$ and heavier hydrocarbons in the bottom of the SRC with the lean solvent stream.

FIG. 1 is a schematic diagram of an ED process, for aromatic hydrocarbons recovery, which employs among other devices, an extractive distillation column (EDC), solvent recovery column (SRC), thermal solvent regenerator (SRG), solvent clean-up column (SCC), and water washing column (WCC). A hydrocarbon feed containing a mixture of aromatic and non-aromatic hydrocarbons is fed via line 41 to the middle portion of the EDC, while a lean solvent from the bottom of the SRC is fed via lines 55, 57, 59 and 71 to near the top of the EDC below the overhead reflux entry point. Suitable extractive solvents include, for example, sulfolane, alkyl-sulfolane, N-formyl morpholine, N-methylpyrrolidone, tetraethylene glycol, triethylene glycol, diethylene glycol, and mixtures thereof, with water as the co-solvent. A preferred solvent comprises sulfolane with water as the co-solvent.

Non-aromatics vapor exiting the top of the EDC through line 42 is condensed in a condenser (not shown) and the condensate is transferred to an overhead receiver D1, which serves to effect a phase separation between the non-aromatic hydrocarbons and the water phases. A portion of the non-aromatic hydrocarbon phase is recycled to the top of the EDC as the reflux via lines 43 and 44 as a second portion is directed to the WWC through lines 45 and 70. The water phase from the overhead receiver D1 in line 49 is combined with water in line 69 from the WWC and the mixture is transferred to a steam generator SR1 via line and 60 to form stripping steam that is introduced into the SRC via line 62 and into the solvent regenerator SRG via line 61. The rich solvent stream containing solvent, aromatic hydrocarbons, and measurable levels of heavy hydrocarbons is withdrawn from the bottom of the EDC via line 46. A portion of the rich solvent is heated in the reboiler R1 and recycled to the bottom of the EDC via line 47 to generate vapor stream in the column, while the rest of the rich solvent is fed to the middle portion of the SRC through line 48.

Stripping steam when injected via line 62 into the lower portion of the SRC assists in the removal of aromatic hydrocarbons from the solvent. An aromatic concentrate, containing water and which is substantially free of solvent and non-aromatic hydrocarbons, is withdrawn through line 50 as an overhead vapor stream from the SRC and after being condensed in a condenser (not shown), the liquid is introduced into an overhead receiver D2. The overhead receiver serves to effect a phase separation between the aromatic hydrocarbons phase and the water phase. A portion of the aromatic hydrocarbon phase from line 51 is recycled to the top of the SRC as the reflux via line 52, while the remaining portion is withdrawn as the aromatic hydrocarbons product through line 53. The water phase is transferred through line 54 to the top of the WWC from where solvent-free non-aromatic products are removed from the top via line 72.

In order to minimize the bottom temperature of the SRC, the receiver D2 is connected to a vacuum source to generate sub-atmospheric conditions in the SRC. A lean solvent stream containing measurable amounts of heavy hydrocarbons is withdrawn from the bottom of the SRC through line 55. The greatest proportion thereof is recycled via lines 57 and 59 and is combined with the solvent phase in line 67 from the SCC to form a lean solvent feed 71 that is supplied to the upper portion of the EDC for extracting the aromatic hydrocarbons in the EDC. A minor portion of the lean solvent is diverted into the SRG via line 58 and steam is introduced into the SRG through line 61, at an entry point below the lean solvent feed entry point. Another minor portion of the lean solvent is heated in the reboiler R2 and recycled to the bottom of the SRC via line 56.

Deteriorated solvent and polymeric sludge are removed as a bottom stream through line 73 while regenerated solvent containing heavy materials (with boiling points below the solvent's boiling point) and substantially all the stripping steam, are recovered as an overhead vapor stream 63. This vapor is combined with the split lean solvent from the bottom of SRC via line 64, containing the solvent, measurable amounts of heavy hydrocarbons and substantially all the stripping steam from SRG to form a mixture that is condensed and cooled in cooler C1 and then introduced via line 65 into the upper portion of the SCC below the location of solvent/hydrocarbon interface. A portion of the raffinate collected from the overhead of the EDC is combined via lines 43 and 45 with the solvent phase in stream 68 from the SCC to form a mixture that is transferred through 70 into the WWC. Another portion of the raffinate is introduced via lines 43 and 66 into the lower portion the SCC, to contact the lean solvent phase counter-currently as the displacement agent to squeeze out the heavy hydrocarbons and polymeric materials from the solvent phase. Optionally, any external benzene-free light hydrocarbon stream can be used effectively as the displacement agent. To minimize the bottom temperature of the SRG, it is preferably operated under reduced pressure (vacuum).

In a preferred application of the ED process depicted in FIG. 1, preferably with sulfolane as the solvent, the temperature of the overhead vapor 63 from the SRG typically ranges from 150° to 200° C., and preferably from 160° to 180° C., under a pressure of 0.1 to 10 atmospheres, and preferably of 0.1 to 0.8 atmospheres. The vapor is cooled in cooler C1 to a temperature approximately from 0 to 100° C., and preferably from 25 to 80° C. The raffinate-to-solvent feed weight ratio in the SCC is typically from 0.1 to 100, and preferably from 0.5 to 10. The contacting temperature in the SCC typically ranges 0° to 100° C., and preferably from 25 to 80° C. The operating pressure of the SCC typically ranges from 1 to 100 atmospheres, and preferably from 1 to 10 atmospheres.

FIG. 2 illustrates an embodiment of the ED process for aromatic hydrocarbons recovery in which clean-up column alone is employed to regenerate the solvent using a light hydrocarbon displacement agent. The high temperature, energy intensive and difficult-to-operate thermal solvent regenerator is eliminated from the solvent regeneration scheme. This process can use the same solvents as for the process shown in FIG. 1. This ED process employs, among other devices, an extractive distillation column (EDC), solvent recovery column (SRC), solvent clean-up column (SCC), and water washing column (WCC).

A hydrocarbon feed containing a mixture of aromatic and non-aromatic hydrocarbons is fed via line 81 to the middle portion of the EDC, while lean solvent in stream 108, that is formed by combining the bottom stream from the SRC via lines 95, 97 and 99 with the solvent stream 105 from the SCC, is fed to near the top of the EDC below the overhead reflux entry point. The lean solvent from the SRC can be filtered with a magnet-assisted filter F1 that removes iron rust particulates and other polymeric sludge that are paramagnetic in nature. Non-aromatics vapor exiting the top of the EDC through line 82 is condensed in a condenser (not shown) and the condensate is transferred to an overhead receiver D1, which serves to effect a phase separation between the non-aromatic hydrocarbons and the water phases. A portion of the non-aromatic hydrocarbon phase in line 83 is recycled to the top of the EDC as the reflux via line 84 while a second portion is directed to the WWC through lines 85 and 107. The water phase from the overhead receiver D1 in line 89 is combined with water in line 100 from the WWC and the mixture is transferred to a steam generator SR1 via line and 102 to form the stripping steam that is introduced into the SRC via line 103, and which assists in the removal of aromatic hydrocarbons from the solvent. The rich solvent stream containing solvent, aromatic hydrocarbons, and measurable amounts heavy hydrocarbons are withdrawn from the bottom of the EDC via line 86. A portion of the rich solvent is heated in the reboiler R1 and recycled to the bottom of the EDC via line 87 to generate vapor stream in the column, while the rest of the rich solvent is fed to the middle portion of the SRC through line 88.

An aromatic concentrate, containing water and which is substantially free of solvent and non-aromatic hydrocarbons, is withdrawn through line 90 as an overhead vapor stream from the SRC and after being condensed in a condenser (not shown), the liquid is introduced into an overhead receiver D2. The overhead receiver serves to effect a phase separation between the aromatic hydrocarbons phase and the water phase. A portion of the aromatic hydrocarbon phase from line 91 is recycled to the top of the SRC as the reflux via line 92, while the remaining portion is withdrawn as the aromatic hydrocarbons product through line 93. The water phase is transferred through line 94 to the top of the WWC and solvent-free non-aromatic products are removed from the top via line 109.

In order to minimize the bottom temperature of the SRC, the receiver D2 is connected to a vacuum source to generate sub-atmospheric conditions in the SRC. A lean solvent stream containing measurable amounts of heavy hydrocarbons is withdrawn from the bottom of the SRC through line 95. The greater proportion thereof is recycled via lines 97 and 99 and is combined with the solvent phase in line 105 from the SCC to form a lean solvent feed 108 that is supplied to the upper portion of the EDC for extracting the aromatic hydrocarbons in the EDC. A minor portion of the lean solvent is diverted through line 98 and cooled in cooler C1 and then introduced via line 101 into the upper portion of the SCC below the location of solvent/hydrocarbon interface. Another minor portion of the lean solvent is heated in the reboiler R2 and recycled to the bottom of the SRC via line 96. A portion of the raffinate collected from the overhead of the EDC is introduced via lines 83 and 104 into the lower portion the SCC, to contact the lean solvent phase counter-currently as the displacement agent to squeeze out the heavy hydrocarbons and polymeric materials from the solvent phase.

The solvent phase from the bottom stream 105 of the SCC, which contains essentially the purified solvent, light non-aromatic displacement agent, and much reduced levels of heavy hydrocarbons and polymeric materials, is continuously withdrawn from lower portion of the SCC and introduced through line 108 as a part of lean solvent feed to the EDC, as a way to recycle the purified solvent into the solvent loop. The minor hydrocarbon phase that accumulates on the top of the SCC and is removed periodically from the overhead of the SCC via line 106 under interface level control, which is then mixed with the raffinate from the overhead of the EDC before being fed via line 107 to the WWC to remove any solvent from the final raffinate product. The solvent clean-up operation may also be conducted in any other continuous multi-stage contacting device, preferably one that is designed for counter-current extraction, such as multi-stage mixers/settlers, or any other rotating type contactors. In the absence of conventional thermal solvent regenerator, filter F1 is preferably installed in the lean solvent line between the SRC and EDC to selectively remove paramagnetic species that are generated from the interaction of decomposed solvent with various solvent additives as well as the heavy hydrocarbons.

In a preferred application of the ED process depicted in FIG. 2, preferably with sulfolane as the solvent, the solvent from the bottom of the SRC is preferably cooled in the cooler C1 to a temperature in the range of approximately 0 to 100° C., and preferably of 25 to 80° C. The raffinate-to-solvent feed weight ratio in the SCC is typically from 0.1 to 100, and preferably from 0.5 to 10. The contacting temperature in the SCC typically ranges from 0 to 100° C., and preferably from 25 to 80° C. The operating pressure of the SCC is typically from 1 to 100 atmospheres, and preferably from 1 to 10 atmospheres.

For both processes illustrated in FIGS. 1 and 2, the operating conditions of the EDC are preferably adjusted to keep substantially all the benzene (the lightest aromatic hydrocarbon) in the bottom of the EDC to maximize its recovery by retaining substantially all $C_{9+}$ hydrocarbons in the bottom of the EDC with the rich solvent (extract) stream. The operating condition of SRC is also modified to strip only $C_8$ and lighter hydrocarbons from the rich solvent stream and to keep substantially all $C_9$ and heavier hydrocarbons in the bottom of the SRC with the lean solvent stream. This is because the $C_{9+}$ hydrocarbons can be recovered from the lean solvent in the solvent clean-up zone.

FIG. 3 is a schematic diagram of a LLE process for aromatic hydrocarbons recovery, which employs among other devices, a liquid-liquid extraction column (LLE), solvent recovery column (SRC), solvent regenerator (SRG), solvent clean-up column (SCC), water washing column (WCC), and extractive stripper column (ESC). The same solvents for the processes depicted in FIGS. 1 and 2 can be employed. Hydrocarbon feed containing a mixture of aromatics and non-aromatics is fed via line 161 to the middle portion of a liquid-liquid extraction column LLE, while lean solvent is introduced near the top of LLE via line 162 to counter-currently contact the hydrocarbon feed. The aromatic hydrocarbons in the feed typically comprise benzene, toluene, ethylbenzene, xylenes, $C_{9+}$ aromatics, and mixtures thereof, and the non-aromatic hydrocarbons typical comprise $C_5$ to $C_{9+}$ paraffins, naphthenes, olefins, and mixtures thereof.

A raffinate phase containing essentially the non-aromatics with a minor amount of solvent is withdrawn from the top of the LLE as stream 163 and a portion thereof is fed to a middle portion of the WWC via line 194 while the remainder portion is directed into the middle of the SCC via line 193. An extract phase from the bottom of the LLE in line 164 is mixed with a secondary lean solvent from line 165; the combined stream 166 is fed to the top of the ESC.

The vapor flow through the ESC is generated by the action of reboiler R1, whereby a portion of the rich solvent in bottom stream 170 is recycled to the ESC via line 171. The reboiler R1 is normally heated by steam at a rate that is sufficient to control the column bottom temperature, the overhead stream composition and the flow rate. Overhead vapor exiting the top of the ESC is condensed in a cooler (not shown) and the condensate is transferred via line 167 to an overhead receiver D1, which serves to effect a phase separation between the hydrocarbon and the water phases. The hydrocarbon phase, containing the non-aromatics and up to 30-40% benzene and heavier aromatics, is recycled to the lower portion of the LLE as reflux via line 169. The water phase is transferred via lines 168 and 187 to steam generator SR1 to generate stripping steam for SRC. Rich solvent consisting of solvent, aromatics free of non-aromatics, and measurable amounts of heavy hydrocarbons and polymeric materials is withdrawn from the bottom of ESC and transferred to the middle portion of SRC via lines 170 and 172. Stripping steam is injected from steam generator SR1 via line 184 into the lower portion of SRC to assist in the removal of aromatic hydrocarbons from the solvent. An aromatic concentrate, containing water and being substantially free of solvent and non-aromatic hydrocarbons, is withdrawn as an overhead vapor stream from SRC and introduced into an overhead receiver D2 via line 173 after being condensed in a cooler (not shown). In order to minimize the bottom temperature of SRC, receiver D2 is connected to a vacuum source to generate sub-atmospheric conditions in the SRC.

Overhead receiver D2 serves to effect a phase separation between the aromatic hydrocarbon and the water phases. A portion of the aromatic hydrocarbon phase in line 174 is recycled to the top of SRC as reflux via line 175, while the remainder portion is withdrawn as aromatic hydrocarbon product through line 176. The water phase that accumulates in the water leg of overhead receiver D2 is fed via line 177 to the WWC as wash water at a location below the interface between the hydrocarbon phase and the water phase near the top of the WWC. The solvent is removed from the LLE raffinate through a counter-current water wash and the solvent-free non-aromatics, which accumulate in the hydrocarbon phase, are then withdrawn from the top of the WWC as solvent-free non-aromatic products through line 185. A water phase, containing the solvent, exits through line 186 from the bottom of the WWC and is combined with line 168, that is the water phase from D1, and fed to steam generator SR1 via line 187 where it is transformed into stripping steam that is introduced into the SRC via line 184 and into the SRG via line 182.

A split stream of the lean solvent from the SRC from lines 178 and 180 is diverted into the SRG via line 181 and steam is introduced into the SRG through line 182, at a location below the lean solvent feed entry point. Another portion of the lean solvent is heated in the reboiler R2 and recycled to the bottom of the SRC via line 179. Deteriorated solvent and polymeric sludge are removed as a bottom stream through line 188, while the regenerated solvent and substantially all the stripping steam, are recovered as an overhead stream 183. A mixture formed of this vapor in line 183 and a split lean solvent from the bottom of SRC in line 189, and which contains solvent, a measurable amount of heavy hydrocarbons and substantially all the stripping steam from the SRG, is condensed and cooled in the cooler C1 and is introduced via line 190 into the upper portion of the SCC below the location of solvent/hydrocarbon interface.

The raffinate containing light non-aromatic displacement agent contacts the solvent phase to squeeze out the heavy hydrocarbons and polymeric materials from the solvent phase into the hydrocarbon phase in the SCC: Optionally, any external benzene-free light hydrocarbon stream can be used effectively as the displacement agent. Solvent phase containing essentially purified solvent, light non-aromatics (the displacement agent), and substantially reduced levels of heavy hydrocarbons is continuously withdrawn from lower portion of the SCC and introduced through lines 191, 195 and 162 into the LLE as a part of the lean solvent feed, as a way to recycle the purified solvent into the solvent loop. The hydrocarbon phase accumulates continuously at the top of the SCC and is removed periodically from the overhead of the SCC via lines 192 under interface level control, which is then mixed with the raffinate from the overhead of the LLE and fed via line 194 to the WWC. The solvent clean-up operation may also be conducted in any other continuous multi-stage contacting device, preferably one that is designed for counter-current extraction, such as multi-stage mixers/settlers, or any other rotating type contactors.

In a preferred application of the LLE process that is depicted in FIG. 3 and preferably with sulfolane as the solvent, the temperature of the overhead vapor from the SRG typically ranges from 150° to 200° C., and preferably from 160° to 180° C., under a pressure of 0.1 to 10 atmospheres, and preferably of 0.1 to 0.8 atmospheres. The mixture comprising of solvent vapor from the SRG and lean solvent from the SRC is condensed and cooled in the cooler C1 to a temperature in the range of approximately 0 to 100° C., and preferably of 25 to 80° C. The raffinate-to-solvent feed weight ratio in the SCC is typically from 0.1 to 100, and preferably from 0.5 to 10. The contacting temperature in the SCC typically ranges from 0° to 100° C., and preferably from 25 to 80° C. The operating pressure of the SCC typically ranges from 1 to 100 atmospheres, and preferably from 1 to 10 atmospheres.

FIG. 4 illustrates a LLE process for aromatic hydrocarbons recovery from the aromatic hydrocarbon and non-aromatic hydrocarbon mixtures, in which a solvent clean-up column alone is employed to regenerate the solvent using a light hydrocarbon displacement agent. The high temperature, energy intensive and difficult-to-operate conventional solvent regenerator is eliminated from the solvent regeneration scheme. This process can use the same solvents as employed in the process shown in FIG. 3. The process as shown employs, among other devices, a liquid-liquid extraction column (LLE), solvent recovery column (SRC), solvent clean-up column (SCC), water washing column (WCC), and extractive stripper column (ESC). Hydrocarbon feed containing a mixture of aromatic and non-aromatics is fed via line 201 to the middle portion of the LLE, while lean solvent is introduced near the top of LLE via line 202 to counter-currently contact the hydrocarbon feed. A raffinate phase in stream 203 containing essentially the non-aromatics with a minor amount of solvent is withdrawn from the top of the LLE and a portion thereof is fed to a middle portion of the WWC via line 227 while the remainder portion is directed into the middle of the SCC via line 223. An extract phase is transferred from the bottom of the LLE via line 204 and is mixed with a secondary lean solvent from line 205; the combined stream 206 is fed to the top of the ESC.

The vapor flow through the ESC is generated by the action of reboiler R1, whereby a portion of the rich solvent in bottom stream 210 is recycled to the ESC via line 211. The reboiler R1 is normally heated by steam at a rate that is sufficient to control the column bottom temperature, the overhead stream composition and the flow rate. Overhead vapor exiting the top of the ESC is condensed in a cooler (not shown) and the condensate is transferred via line 207 to an overhead receiver D1, which serves to effect a phase separation between the hydrocarbon and the water phases. The hydrocarbon phase, containing the non-aromatics and up to 30-40% benzene and heavier aromatics, is recycled to the lower portion of the LLE as reflux via line 209. The water phase is transferred via lines 208 and 226 to steam generator SR1 to generate stripping steam for SRC. Rich solvent consisting of solvent, purified aromatics, and measurable amounts of heavy hydrocarbons and polymeric materials is withdrawn from the bottom of ESC and transferred to the middle portion of SRC via lines 210 and 212. Stripping steam is injected from steam generator SR1 via line 234 into the lower portion of SRC to assist in the removal of aromatic hydrocarbons from the solvent. An aromatic concentrate, containing water and being substantially free of solvent and non-aromatic hydrocarbons, is withdrawn as an overhead vapor stream from the SRC and introduced into an overhead receiver D2 via line 213 after being condensed in a cooler (not shown). In order to minimize the bottom temperature of SRC, receiver D2 is connected to a vacuum source to generate sub-atmospheric conditions in SRC.

Overhead receiver D2 serves to effect a phase separation between the aromatic hydrocarbon and the water phases. A portion of the aromatic hydrocarbon phase in line 214 is recycled to the top of the SRC as reflux via line 215, while the remainder portion is withdrawn as aromatic hydrocarbon product through line 216. The water phase that accumulates in the water leg of overhead receiver D2 is fed via line 217 to the WWC as wash water at a location below the interface between the hydrocarbon phase and the water phase near the top of the WWC. Solvent is removed from the LLE raffinate through a counter-current water wash and the solvent-free non-aromatics, which accumulate in the hydrocarbon phase, are withdrawn from the top of the WWC as solvent-free non-aromatic products through line 228. A water phase, containing the solvent, exits through line 235 from the bottom of the WWC and is combined with line 208 that is the water phase from D1 and is fed to steam generator SR1 via line 226 where it is transformed into stripping steam that is introduced into SRC via line 234.

A split stream 221 of the lean solvent from the SRC in lines 218 and 220 is condensed and cooled in the cooler C1 and then introduced via line 222 into the upper portion of the SCC below the location of the solvent/hydrocarbon interface. Another portion of the lean solvent is heated in the reboiler R2 and recycled to the bottom of the SRC via line 219. Preferably, the majority of the lean solvent exiting from the bottom of the SRC in line 218 is transferred into the LLC via line 202.

The raffinate that contains the light non-aromatic displacement agent contacts the solvent phase to squeeze out the heavy hydrocarbons and polymeric materials from the solvent phase into the hydrocarbon phase in the SCC. A solvent phase, that contains essentially purified solvent, light non-aromatics (the displacement agents), and substantially reduced levels of heavy hydrocarbons, is continuously withdrawn from lower portion of the SCC and introduced through lines 224, 229 and 202 into the LLE as a part of the lean solvent feed, as a way to recycle the purified solvent into the solvent loop. A filter F1 that is enhanced with a magnetic field is preferably installed in line 229 to remove paramagnetic species that is generated from the interaction of decomposed solvent with various solvent additives as well as the heavy hydrocarbons.

The hydrocarbon phase which accumulates continuously at the top of the SCC and is removed periodically from the overhead of the SCC via line 225 under interface level control, which is then mixed with the raffinate from the overhead of the LLE before being fed via line 227 to the WWC where any solvent from the final raffinate product is removed.

In a preferred application of the LLE process that is depicted in FIG. 4 preferably with sulfolane as the solvent, preferably the portion of the lean solvent that withdrawn from the bottom of the SRC and directed to cooler C1 is cooled to a temperature typically in the range of approximately 0 to 100° C., and preferably of 25 to 80° C. In addition, the raffinate-to-solvent feed weight ratio in the SCC typically ranges from 0.1 to 100, and preferably from 0.5 to 10. The contacting temperature in the SCC typically ranges 0 to 100° C., and preferably from 25 to 80° C. The operating pressure of the SCC typically is from 1 to 100 atmospheres, and preferably from 1 to 10 atmospheres.

EXAMPLES

The following examples are presented to further illustrate different aspects and embodiments of the invention and are not to be considered as limiting the scope of the invention.

The aromatic hydrocarbons recovery process that employs the extractive distillation process as shown in FIG. 1 was tested at a plant facility. To confirm the effectiveness of using light, less-polar hydrocarbons as displacement agents for removing heavy hydrocarbons and polymeric materials from a lean solvent, samples the raffinate from the overhead of the extractive distillation column and the lean solvent that is supplied to the solvent clean-up column were tested and analyzed.

Example 1

A sample of the raffinate from the overhead stream of the EDC, which corresponds to line 66 in FIG. 1, was withdrawn and analyzed. The Paraffinic Olefinic Napthenic and Aromatic (PONA) analysis of the sample is summarized as follows.

TABLE 1

Analysis of ED Raffinate Reported by Group Type and Carbon Number (Wt %)

| | n-Paraffins | i-Paraffins | Olefins | Naphthenes | Aromatics | Total |
|---|---|---|---|---|---|---|
| $C_5$ | 1.00 | 0.89 | 0.02 | 0 | 0 | 1.91 |
| $C_6$ | 15.63 | 24.90 | 0.17 | 19.23 | 0.65 (Benzene) | 60.58 |
| $C_7$ | 4.29 | 15.71 | 0.06 | 8.33 | 0 | 28.39 |
| $C_8$ | 1.27 | 2.07 | 0.16 | 2.29 | 0 | 5.79 |
| $C_9$ | 0.30 | 1.14 | 0.01 | 0.22 | 0 | 1.67 |

TABLE 1-continued

Analysis of ED Raffinate Reported by Group Type and Carbon Number (Wt %)

| | n-Paraffins | i-Paraffins | Olefins | Naphthenes | Aromatics | Total |
|---|---|---|---|---|---|---|
| $C_{10}$ | 0 | 0.02 | 0 | 0 | 0 | 0.02 |
| Total Unknown Hydrocarbons | | | | | | 1.53 |
| Heavy Hydrocarbons | | | | | | 0.11 |
| Total | | | | | | 100.00 |

The data in Table 1 demonstrate that the major components in the EDC raffinate were the less polar hydrocarbons in the $C_6$-$C_7$ range and the minor components were in the $C_8$-$C_9$ range.

Lean solvent containing sulfolane from line 65 in FIG. 1 was also tested and found to comprise 1.4 wt % of the heavy hydrocarbons and polymeric materials. The PONA analysis of this solvent sample is summarized in the following table.

TABLE 2

Analysis of the Lean Solvent Reported by Group Type and Carbon Number (Wt %)

| | n-Paraffins | i-Paraffins | Olefins | Naphthenes | Aromatics | Total |
|---|---|---|---|---|---|---|
| $C_7$ | 0 | 0 | 0 | 0 | 0.007 | 0.007 |
| $C_8$ | 0 | 0 | 0 | 0 | 0.001 | 0.001 |
| $C_9$ | 0 | 0 | 0 | 0 | 0.004 | 0.004 |
| $C_{10}$ | 0 | 0 | 0 | 0.003 | 0.001 | 0.004 |
| $C_{11}$ | 0 | 0 | 0 | 0 | 0.015 | 0.015 |
| $C_{12}$ | 0 | 0 | 0 | 0 | 0.014 | 0.014 |
| $C_{13}$ | 0 | 0.004 | 0.006 | 0 | 0 | 0.010 |
| $C_{14}$ | 0.050 | 0 | 0 | 0 | 0 | 0.050 |
| Total Heavy Hydrocarbons | | | | | | 1.122 |
| Total Heavy Unknown | | | | | | 0.335 |
| Solvent (Sulfolane) | | | | | | 98.438 |
| Total | | | | | | 100.000 |

Figure 5:
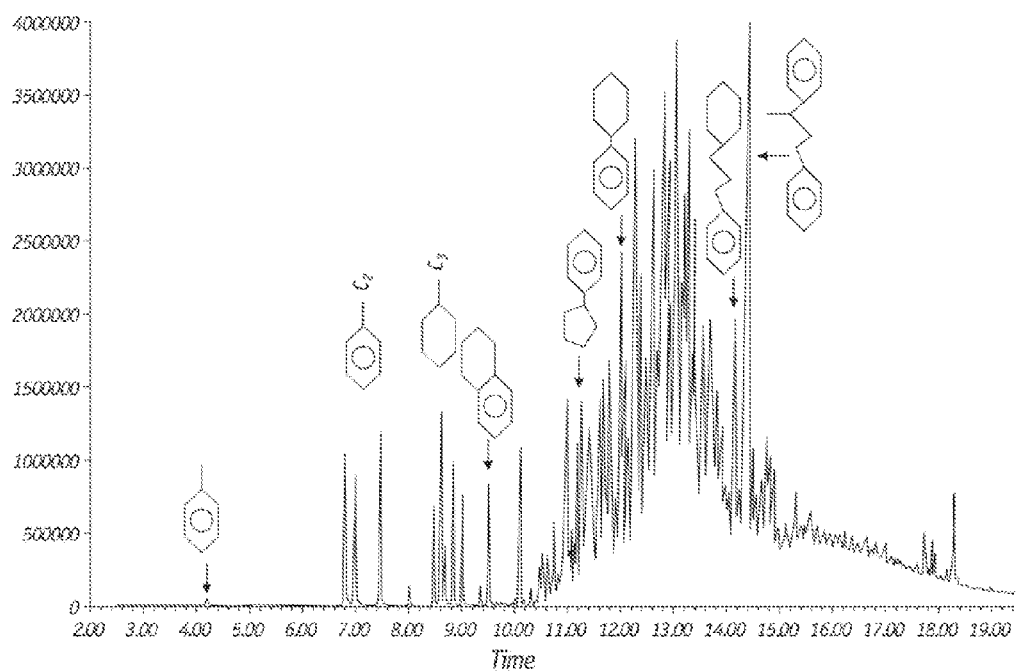
FIG. 5 is a chromatogram from a GC/MS analysis of the heavy hydrocarbon components and polymeric materials in a lean sulfolane solvent sample used in an aromatic hydrocarbons recovery process.

The results shown in Table 2 indicate that roughly all of the identifiable $C_7$ to $C_{14}$ hydrocarbons in the lean solvent were aromatics. To identify the species in the heavy hydrocarbons and polymeric materials, the same lean solvent sample was analyzed using gas chromatography-mass spectrometry (GC/MS) methods and the chromatogram of heavy hydrocarbons and unknowns of the lean solvent sample is presented in FIG. 5. As expected, only a few of the heavy hydrocarbons species can be identified by their molecular structures. Nevertheless, FIG. 5 does establish the critical finding that the major portion of the heavy hydrocarbons consisted of multi-non-condensed ring aromatic compounds that are heavier than $C_{12}$ hydrocarbons. Without being limiting to a particular theory, it is believed that the heavies were formed in reactions whereby individual aromatic rings were connected by aliphatic chains. The reactions were induced by prolonged elevated thermal conditions in the lean solvent.

Example 2

Samples of lean solvent were mixed with samples of raffinate (the displacement agent) under different raffinate-to-solvent weight ratios (R/S), to measure the capability of the displacement agent in removing the heavy hydrocarbons and polymeric materials from the solvent. The solvent and raffinate samples had the same compositional makeup as those of Example 1. Solvent and raffinate were thoroughly mixed in a vessel at room temperature by rigorous shaken. The hydrocarbon phase and the solvent phase were allowed to separate for 30 minutes, although clear phase separation was observed immediately once the shaken stopped. Results of the laboratory extraction tests are summarized in Table 3.

TABLE 3

Mass Balance of the Laboratory Extraction (displacement) Test

| | Before Displacement Test | | After Displacement Test | |
| --- | --- | --- | --- | --- |
| R/S | Solvent Feed (g) | Raffinate Feed (g) | Solvent Phase (g) | Hydrocarbon Phase (g) |
| 1.0 | 100.0 | 100.0 | 99.5 | 100.5 |
| 2.0 | 100.0 | 200.0 | 99.1 | 200.6 |
| 3.0 | 100.0 | 300.1 | 98.3 | 301.7 |

The data in Table 3 show that the total weight increase of the hydrocarbon phase (or total weight decrease of the solvent phase) is proportional to the R/S (the amount of raffinate used). Since the raffinate feed included a substantial amount of the non-aromatic hydrocarbons, the raffinate was not very soluble in the sulfolane solvent and vice versa. As a result, it is believed that mass transfer between the two phases was driven by the dissolution of the raffinate (the displacement agent) into the solvent phase and the concomitant displacement of the heavy hydrocarbons and polymeric materials from the solvent phase, on a molecule-to-molecule basis. The molecular weight of the heavy hydrocarbons and polymeric materials are significantly higher than those of the species in the raffinate, so it is believed that the weight gain in the hydrocarbon phase is due to the weight difference of incoming heavies minus the outgoing species of raffinate (the displacement agent) on a molecule-to-molecule basis. In other words, the test shows that displacement of heavy hydrocarbons and polymer materials from the lean solvent by the species in the raffinate occurred through phase contact.

Example 3

To confirm the conclusions derived from the results in Example 2, lean solvent samples before and after contacting the raffinate (which corresponds to the lean solvent feed and the solvent phase after raffinate contact), under a R/S of 3.0, were analyzed by GC/MS. Chromatograms of both solvent samples were also obtained. The chromatogram of the lean solvent sample prior to contact with the raffinate showed the sulfolane peak as the major component in the solvent appears in 21 through 23 minutes (marked at 22.1 minutes) in the GC elusion time. Several important heavy hydrocarbon components having boiling points lower than that of sulfolane appeared at 12.5, 12.9, 13.9, 16.2, 16.4, 17.0, 18.5 and 20.2 minutes in elusion time, while those having boiling points higher than sulfolane appear from 23 to 31 minutes in elusion time.

After contacting the lean solvent with the raffinate (the displacement agent), these heavy hydrocarbon peaks were substantially disappeared in the solvent phase. In particular, the chromatogram showed that, after contacting the raffinate, the solvent phase contained substantially only the species from the raffinate (the displacement agent) with peaks appearing 1.9 to 7.1 minutes in elusion time. This result was unexpected and surprising as it demonstrated that the raffinate was extremely effective in displacing the heavy hydrocarbons from the sulfolane solvent even when contacting the raffinate only once at ambient conditions.

Example 4

In this example, the mass of the individual heavy hydrocarbon species in the lean solvent was measured before and after the solvent contacted the raffinate at a R/S of 3.0. The differences in mass provided a determination of the removal efficiency for the individual species as tabulated Table 4.

TABLE 4

Efficiency for Individual Heavy Hydrocarbon Species Removal by Raffinate As Displacement Agent

| Species Elusion Time (Minute) | Before Displacement Amount (g) | After Displacement Amount (g) | % of Removal |
| --- | --- | --- | --- |
| 12.5 | 0.0632 | 0.0090 | 85.7 |
| 12.9 | 0.0465 | 0.0050 | 89.3 |
| 13.9 | 0.0833 | 0.0100 | 88.0 |
| 16.2 | 0.0211 | 0.0014 | 93.4 |
| 16.5 | 0.0526 | 0.0036 | 93.2 |
| 16.5 | 0.0213 | 0.0014 | 93.6 |
| 17.0 | 0.0233 | 0.0021 | 91.1 |
| 22.1 (Sulfolane) | 98.6539 | 94.8825 | 3.8 |
| 24.5 | 0.0223 | 0.0010 | 95.3 |
| 25.1 | 0.0346 | 0.0017 | 95.0 |
| 25.9 | 0.0269 | 0.0024 | 91.0 |
| 26.0 | 0.0248 | 0.0024 | 90.2 |
| 26.3 | 0.0389 | 0.0033 | 91.6 |
| 26.9 | 0.0565 | 0.0027 | 95.1 |
| 27.5 | 0.0252 | 0.0000 | 100.0 |
| 30.9 | 0.1524 | 0.0183 | 88.0 |

The results shown in Table 4 demonstrate that the raffinate (the light hydrocarbon displacement agent) was very effective in displacing essentially all of the heavy hydrocarbons and polymeric materials (with boiling point higher or lower than that of the solvent) from the lean solvent. In a one-stage extraction at room temperature, the raffinate displaced 86 to 95% of the heavy species from the solvent. It is expected that the heavy hydrocarbons and polymeric materials can be completely removed from the lean solvent by employing a few more extraction stages without any significant energy expenditure.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A method for recovering a polar hydrocarbon selective solvent substantially free of hydrocarbons and other impurities from a solvent-rich stream containing the selective solvent, measurable amounts of heavy aromatic hydrocarbons, and polymeric materials generated from reactions among thermally decomposed or oxidized solvent, heavy aromatic hydrocarbons, and additives, which method comprises the steps of:
   (a) introducing a feed containing polar and less polar hydrocarbons into a middle portion of an extractive distillation column (EDC) and introducing a solvent-rich stream into an upper portion of the EDC as a selective solvent feed;

(b) recovering a water-containing, less polar hydrocarbon-rich stream from a top of the EDC and withdrawing a first solvent-rich stream containing solvent and polar hydrocarbons from a bottom of the EDC;

(c) introducing the first solvent-rich stream into a middle portion of a solvent recovery column (SRC), recovering a polar hydrocarbon-rich stream, that is substantially free of solvent and less polar hydrocarbons, from a top of the SRC, and removing a second solvent-rich stream from a bottom of the SRC;

(d) introducing a first portion of the second solvent-rich stream into the upper portion of the EDC in step (a) as the selective solvent feed;

(e) cooling a second portion of the second solvent-rich stream in step (c) and introducing the cooled second portion of the solvent-rich stream into an upper portion of a solvent cleanup zone to form a solvent phase;

(f) introducing a light non-aromatic hydrocarbon-rich stream into a lower portion of the solvent cleanup zone, as a heavy aromatic hydrocarbon displacement agent, to squeeze out heavy aromatic hydrocarbons and polymeric materials from the solvent phase into a hydrocarbon phase;

(g) withdrawing an accumulated hydrocarbon phase containing heavy aromatic hydrocarbons and polymeric materials from an upper portion of the solvent cleanup zone, and recovering a solvent phase containing solvent and light non-aromatic hydrocarbons, which serve as heavy aromatic hydrocarbon displacement agents, and having substantially reduced levels of heavy aromatic hydrocarbons and polymeric materials, from a lower portion of the solvent cleanup zone; and (h) introducing the solvent phase from the solvent cleanup zone in step (g) into an upper portion of the EDC in step (a) as part of a selective solvent feed to recycle purified solvent into a solvent loop.

2. The method of claim 1 wherein in step (d) the second solvent-rich stream is filtered through an in-line filter that is enhanced with a magnetic field before entering the upper portion of the EDC.

3. The method of claim 1 wherein the polar hydrocarbons are aromatic and said less polar hydrocarbons are paraffinic, naphthenic, and olefinic.

4. The method of claim 1 wherein the solvent is selected from the group consisting of sulfolane, alkyl-sulfolane, N-formyl morpholine, N-methyl pyrrolidone, tetraethylene glycol, triethylene glycol, diethylene glycol, and mixtures thereof, with water as the co-solvent.

5. The method of claim 1 wherein the solvent comprises sulfolane with water as the co-solvent.

6. The method of claim 1 wherein the solvent is N-formyl morpholine.

7. The method of claim 1 wherein the light hydrocarbon-rich stream is the less polar hydrocarbon-rich stream from overhead of the EDC.

8. The method of claim 1 wherein the light non-aromatic hydrocarbon-rich stream is an external benzene-free stream containing $C_5$-$C_8$ hydrocarbons.

9. The method of claim 1 wherein the EDC is operated under such conditions as to maximize the benzene recovery in the first solvent-rich stream by keeping substantially all $C_{9+}$ hydrocarbons in the first solvent-rich stream.

10. The method of claim 1 wherein the SRC is operated under such conditions as to strip only $C_8$ and lighter hydrocarbons from the first solvent-rich stream and to keep substantially all $C_9$ and heavier hydrocarbons in the second solvent-rich stream.

11. The method of claim 1 wherein step (d) comprises introducing a greater portion of the second solvent-rich stream into an upper portion of a EDC and introducing a first minor portion of the second solvent-rich stream into an upper portion of the thermal solvent regeneration zone, recovering a third solvent-rich stream containing solvent, water, and hydrocarbons and other compounds having boiling points below that of the solvent, from a top of the solvent regeneration zone, and removing heavy sludge from a lower portion of the solvent regeneration zone and wherein step (e) comprises cooling a mixture that comprises the third solvent-rich stream in step (d) and a second minor portion of the second solvent-rich stream in step (c) and introducing the mixture into an upper portion of the solvent cleanup zone to form a solvent phase.

12. The method of claim 11 wherein the polar hydrocarbons are aromatic and said less polar hydrocarbons are paraffinic, naphthenic, and olefinic.

13. The method of claim 11 wherein the solvent is selected from the group consisting of sulfolane, alkyl-sulfolane, N-formyl morpholine, N-methyl pyrrolidone, tetraethylene glycol, triethylene glycol, diethylene glycol, and mixtures thereof, with water as the co-solvent.

14. The method of claim 11 wherein the solvent comprises sulfolane with water as the co-solvent.

15. The method of claim 11 wherein the solvent is N-formyl morpholine.

16. The method of claim 11 wherein the light non-aromatic hydrocarbon-rich stream is the less polar hydrocarbon-rich stream from overhead of the EDC.

17. The method of claim 11 wherein the light non-aromatic hydrocarbon-rich stream is an external benzene-free stream containing $C_5$-$C_8$ hydrocarbons.

18. The method of claim 11 wherein the EDC is operated under such conditions as to maximize the benzene recovery in the first solvent-rich stream by keeping substantially all $C_{9+}$ hydrocarbons in the first solvent-rich stream.

19. The method of claim 11 wherein the SRC is operated under such conditions as to strip only $C_8$ and lighter hydrocarbons from the first solvent-rich stream and to keep substantially all $C_9$ and heavier hydrocarbons in the second solvent-rich stream.

20. A method for recovering a polar hydrocarbon selective solvent substantially free of hydrocarbons and other impurities from a solvent-rich stream containing the selective solvent, measurable amount of heavy aromatic hydrocarbons, and polymeric materials generated from reactions among thermally decomposed or oxidized solvent, heavy aromatic hydrocarbons, and additives, which method comprises the steps of:

(a) introducing a feed containing polar and less polar hydrocarbons into a middle portion of a liquid-liquid extraction column (LLE) and introducing a solvent-rich stream into an upper portion of the LLE as a selective solvent feed;

(b) recovering a water-containing, less polar hydrocarbon-rich stream from a top of the LLE and withdrawing the first solvent-rich stream containing solvent, polar hydrocarbons and minor amounts of less polar hydrocarbons from a bottom of the LLE;

(c) introducing a mixture of comprising the first solvent-rich stream and a minor portion of a third solvent-rich stream from a bottom of a solvent recovery column (SRC), into an upper portion of an extractive stripping column (ESC), recovering a hydrocarbon-rich, vapor containing less polar hydrocarbons and a significant amount of benzene and heavier aromatics, which is condensed and recycled to a lower portion of LLE as the reflux, and withdrawing a second solvent-rich stream containing solvent and polar hydrocarbons, which is substantially free of less polar hydrocarbons, from a bottom of the ESC;

(d) introducing the second solvent-rich stream in step (c) into a middle portion of the SRC, withdrawing a polar hydrocarbon-rich stream, which is substantially free of solvent and non-polar hydrocarbons, from a top of the SRC, and removing a third solvent-rich stream from the bottom of the SRC;

(e) introducing a portion of the third solvent-rich stream into the upper portion of the LLE in step (a) as the selective solvent feed;

(f.) cooling a minor portion of the third solvent-rich stream in step (d) and introducing the cooled minor portion of the third solvent-rich stream into an upper portion of a solvent cleanup zone to form a solvent phase;

(g) introducing a light non-aromatic hydrocarbon-rich stream into a lower portion of the solvent clean-up zone, as a heavy aromatic hydrocarbon displacement agent, to squeeze out heavy aromatic hydrocarbons and polymeric materials from the solvent phase into a hydrocarbon phase;

(h) withdrawing an accumulated hydrocarbon phase containing heavy aromatic hydrocarbons and polymeric materials from an upper portion of the solvent clean-up zone and recovering the solvent phase containing solvent, light non-aromatic hydrocarbons, which serve as heavy aromatic hydrocarbon displacement agents, and having substantially reduced levels of heavy aromatic hydrocarbons and polymeric materials, from a lower portion of the solvent clean-up zone; and (i) introducing the solvent phase from the solvent clean-up zone in step (h) into an upper portion of the LLE in step (a) as part of a selective solvent feed to recycle purified solvent into a solvent loop.

21. The method of claim 20 wherein in step (e) the third solvent-rich stream is filtered through an in-line filter that is enhanced with a magnetic field before entering the upper portion of the LLE.

22. The method of claim 20 wherein the polar hydrocarbons are aromatic and said less polar hydrocarbons are paraffinic, naphthenic, and olefinic.

23. The method of claim 20 wherein the solvent is selected from the group consisting of sulfolane, alkyl-sulfolane, N-formyl morpholine, N-methylpyrrolidone, tetraethylene glycol, triethylene glycol, diethylene glycol, and mixtures thereof, with water as the co-solvent.

24. The method of claim 20 wherein the solvent comprises sulfolane with water as the co-solvent.

25. The method of claim 20 wherein the solvent is tetraethylene glycol with water as the co-solvent.

26. The method of claim 20 wherein the light non-aromatic hydrocarbon-rich stream is the less polar hydrocarbon-rich stream from overhead of the LLE.

27. The method of claim 20 wherein the light non-aromatic hydrocarbon-rich stream is an external benzene-free stream containing $C_5$-$C_8$ hydrocarbons.

28. The method of claim 20 wherein step (e) comprises introducing a greater portion of the third solvent-rich stream into the upper portion of the LLE in step (a) and introducing a first minor portion of the third solvent-rich stream into an upper portion of a high-temperature thermal solvent regeneration zone, recovering a fourth solvent-rich stream containing solvent, water, and hydrocarbons and other compounds having boiling points below that of the solvent, from a top of the solvent regeneration zone, and removing heavy sludge from a lower portion of the solvent regeneration zone and wherein step (f) comprises cooling a mixture comprising the fourth solvent-rich stream in step (e) and a second minor portion of the third solvent-rich stream in step (d) and introducing the mixture into an upper portion of the solvent cleanup zone to form a solvent phase.

29. The method of claim 28 wherein the polar hydrocarbons are aromatic and said less polar hydrocarbons are paraffinic, naphthenic, and olefinic.

30. The method of claim 28 wherein the solvent is selected from the group consisting of sulfolane, alkyl-sulfolane, N-formyl morpholine, N-methylpyrrolidone, tetraethylene glycol, triethylene glycol, diethylene glycol, and mixtures thereof, with water as the co-solvent.

31. The method of claim 28 wherein the solvent comprises sulfolane with water as the co-solvent.

32. The method of claim 28 wherein the solvent is tetraethylene glycol with water as the co-solvent.

33. The method of claim 28 wherein the light non-aromatic hydrocarbon-rich stream is the less polar hydrocarbon-rich stream from overhead of the LLC.

34. The method of claim 28 wherein the light non-aromatic hydrocarbon-rich stream is an external benzene-free stream containing $C_5$-$C_8$ hydrocarbons.

* * * * *